United States Patent [19]
Cuntze et al.

[11] 4,185,098
[45] Jan. 22, 1980

[54] DISINFECTANT

[75] Inventors: Ulrich Cuntze, Hofheim am Taunus; Wolfgang Raether, Dreieich; Bernhard Reul, Königstein; Gerhard Ross, Hofheim am Taunus, all of Fed. Rep. of Germany

[73] Assignee: Hoechst Aktiengesellschaft, Frankfurt am Main, Fed. Rep. of Germany

[21] Appl. No.: 787,205

[22] Filed: Apr. 13, 1977

[30] Foreign Application Priority Data

Apr. 15, 1976 [DE] Fed. Rep. of Germany ....... 2616713

[51] Int. Cl.² .................. A01N 9/02; A01N 9/20; A01N 9/30; A01N 9/36
[52] U.S. Cl. .................. 424/199; 424/251; 424/273 R; 424/320; 424/325
[58] Field of Search ................. 424/199, 320

[56] References Cited

U.S. PATENT DOCUMENTS 2,459,062  1/1949  Cooti et al. ............... 424/320

FOREIGN PATENT DOCUMENTS 2319045  8/1975  Fed. Rep. of Germany.
783882  10/1957  United Kingdom .............. 424/320

*Primary Examiner*—Allen J. Robinson
*Attorney, Agent, or Firm*—Curtis, Morris & Safford

[57] ABSTRACT

Disinfectants which are characterized in that they contain a mixture of a compound of the formula I $$H-\overset{O}{\underset{O^{\ominus}}{\overset{\|}{P}}}-O-CH-\overset{R^2}{\underset{R^1}{\overset{|}{C}}}-CH_2\overset{\oplus}{\underset{R^3}{\overset{R^4}{\underset{|}{N}}}}-\left[(CH_2)_n-\overset{R^6}{\underset{R^5}{\overset{|}{N}}}\right]_m-R^7 \quad I$$

in which
  $R^1$ represents a hydrogen atom or a methyl group,
  $R^2$, $R^3$, $R^4$, $R^5$ and $R^6$, which may be identical or different, each represent a hydrogen atom or an alkyl radical having of from 1 to 4 carbon atoms, $R^7$ represents an alkyl or alkenyl group having from 8 to 18 carbon atoms,
  n is 2 or 3 and
  m is zero or an integer from 1 to 4, in admixture with one or more chlorinated hydrocarbons or with non chlorinated aromatic hydrocarbons and a compound of the formula II $$R^8-\underset{(CH_2)_v}{\overset{(C_2H_4-O)_x-H}{\underset{|}{N}}}-N\underset{(C_2H_4-O)_z-H}{\overset{(C_2H_4-O)_y-H}{\diagup}} \quad II$$

or of the formula III $$R^9-\overset{O}{\overset{\|}{C}}-NH-(CH_2)_v-N\overset{R^{10}}{\underset{R^{11}}{\diagup}} \quad III$$

or of the formula IV $$R^9-C\underset{\underset{(C_2H_4-O)_q-H}{\overset{|}{R^1}}}{\overset{N-CH_2}{\diagdown}}\underset{N-CH}{\overset{}{\diagup}}(CH_2)_p \quad IV$$

or a mixture of compounds of the formulae II to IV, in which
  $R^8$ represents an alkyl or alkenyl radical having from 8 to 18 carbon atoms,
  $R^9$ represents an alkyl or alkenyl radical having from 7 to 17 carbon atoms;
  $R^{10}$ represents a hydrogen atom, a methyl or ethyl group,
  $R^{11}$ represents methyl or ethyl,
  x, y and z each represent an integer from zero to 2,
  v is 2 or 3,
  p is zero or 1 and
  q is zero or 1.

5 Claims, No Drawings

DISINFECTANT

The present invention relates to a disinfectant, which is effective against pathogenic bacteria, viruses, fungi, helminthic ova and the oocysts of protozoa, especially the oocysts of different species of coccidia. It is used especially for the disinfection of stables, outbuildings and kennels.

Coccidia, the pathogenic bacteria of coccidiosis, are protozoa which may be found in all species of fowls, in other birds and in a great number of domestic and commercially reared animals, especially rabbits, sheep, cattle, dogs and cats.

Oocysta having solid protective walls are generally hard to kill by disinfective substances because the usual disinfectants cannot penetrate into the interior of these permanent forms. This is especially true in the case of oocysts of coccidia, which are especially well protected against all the usual disinfective substances by their lipid-containing keratin walls.

Commercial disinfectants contain the following substances as active ingredients against oocysts of coccidia, as individual components or as mixtures: phenolic soaps, sodium hypochloride in admixture with sodium hydroxide solution, carbon disulfide, chlorinated lime, phenols, chlorophenols, cresols, chlorocresols, cresolsulfonic acids, cresol soaps, coal tar oils, resin soaps, chlorothymol, iodine (colloidal) and others (cf. Deutsche Tierarztliche Wochenschrift 80, 23, pages 541–564 (1973)).

As solvents for these disinfectant preparations there are mainly used chlorinated hydrocarbons, in most cases with the addition of emulsifiers, to produce a homogeneous dispersion of the disinfectant when diluting it with water to the required concentration to be applied.

A certain number of substances that kill oocysts are known, for example carbon disulfide, cresol, chloroform and methylene chloride, but practically all of these substances need too long a period of time and too high a concentration to achieve effective destruction of the organisms.

One exception to the usual long period of action is carbon disulfide. This compound, however, at the required concentration to be applied, has considerable disadvantages, for example in its toxicity to humans and animals, its strong odor, its combustibility which involves the danger of fires and the formation of explosive mixtures, and in difficulty in its processing in industry.

German Auslegschrift No. 2,319,045 provides disinfectants which are characterized in that they contain a mixture of a compound of the formula I $$H-\overset{O}{\underset{O^{\ominus}}{P}}-O-CH-\underset{R^1}{\overset{R^2}{\underset{|}{C}}}-CH_2 \overset{\oplus}{\underset{R^5}{\underset{|}{N}}}\left[-(CH_2)_n-\underset{|}{N}\right]_m R^7 \quad I$$

in which
R¹ represents a hydrogen atom or a methyl group,
R², R³, R⁴, R⁵ and R⁶, which may be identical or different, each represent a hydrogen atom or an alkyl radical of from 1 to 4 carbon atoms,
R⁷ represents an alkyl or alkenyl group having from 8 to 18 carbon atoms,
n is 2 or 3 and
m is an integer from 0 to 4, in admixture with one or more chlorinated hydrocarbons.

Suitable chlorinated hydrocarbons are aliphatic compounds, especially low molecular weight alkanes or alkenes bearing one or several chlorine atoms, for example methylene chloride, chloroform, carbon tetrachloride, ethylene chloride, trichloroethane, tetrachloroethane or tetrachloroethylene, furthermore chlorinated aromatic compounds, for example chlorobenzene, dichlorobenzene, trichlorobenzene, tetrachlorobenzene, or a mixture of different chlorinated hydrocarbons.

The disinfectants are advantageously diluted with water to a content of active matter of from 0.25 to 10% by weight, prior to being applied.

The mixtures prepared have a high disinfective action against pathogenic bacteria, fungi, worm ova and a number of viruses, and especially against permanent forms of oocysts.

It has now been found that the disinfective action, especially against oocysts of coccidia, of the disinfectant disclosed in the above patent application, can be improved considerably by adding to the compound of the formula I a compound of the formula II $$R^8-\underset{|}{N}-(CH_2)_v-N\underset{\diagdown (C_2H_4-O)_z-H}{\overset{\diagup (C_2H_4-O)_y-H}{\diagup}} \quad II$$
$$\quad\quad (C_2H_4-O)_x-H$$

or of the formula III $$R^9-\overset{O}{\underset{}{C}}-NH-(CH_2)_v-N\underset{\diagdown R^{11}}{\overset{\diagup R^{10}}{\diagup}} \quad III$$

or of the formula IV $$R^9-C\underset{\diagdown N-CH}{\overset{\diagup N=CH_2}{\diagup}}\underset{\overset{|}{(C_2H_4-O)_q-H}}{\overset{|}{R^1}}(CH_2)_p \quad IV$$

or a mixture of any of the compounds of the formulae II to IV, in which
R⁸ represents an alkyl or alkenyl radical having from 8 to 18 carbon atoms,
R⁹ represents an alkyl or alkenyl radical having from 7 to 17 carbon atoms,
R¹⁰ represents a hydrogen atom, a methyl or ethyl group,
R¹¹ represents methyl or ethyl
x, y and z each represent an integer from zero to 2,
v is 2 or 3,
p is zero or 1 and
q is zero or 1.

Furthermore, in addition to or instead of chlorinated hydrocarbons, aromatic hydrocarbons may be used as components of the mixture.

R⁸ preferably stands for an alkyl or alkenyl radical having from 12 to 16 carbon atoms, and R⁹ preferably stands for an alkyl or alkenyl radical having from 11 to 17 carbon atoms.

Suitable compounds of the formula II are, for example, tallow fat propylene diamine, coconut propylene diamine, lauryl ethylene diamine, lauroy propylene diamine or the triethoxy, tetraethoxy or hexaethoxy derivatives of these compounds.

Preferred compound of the formula III are especially the following amines:

N,N-dimethyl-N-(3-lauroylamidopropyl)-amine,
N,N-diethyl-N-(2-oleylamidoethyl)-amine,
N,N-diethyl-N-(2-lauroylamidoethyl)-amine,
N,N-dimethyl-N-(3-coconutalkylamidopropyl)-amine,
N,N-dimethyl-N-(3-tallow fatalkylamidopropyl)-amine,
N,N-dimethyl-N-(3-oleylamidopropyl)-amine,
N,N-dimethyl-N-(2-lauroylamidoethyl)-amine,
N,N-dimethyl-N-(2-oleylamidoethyl)-amine,
N,N-diethyl-N-(3-lauroylamidopropyl)-amine,
N,N-diethyl-N-(3-oleylamidopropyl)-amine,
N,N-diethyl-N-(2-coconutalkylamidoethyl)-amine.

The following compounds are preferably used among compounds of the formula IV: 2-undecyl-imidazoline, 2-oleyl-imidazoline, 2-undecyl-tetrahydropyrimidine, 2-oleyltetrahydropyrimidine, 2-heptadecyl imidazoline, 2-undecyl-4-methyl-imidazoline, 2-heptadecyl-4-methyl-imidazoline, 2-undecyl-3-hydroxyethyl-imidazoline, 2-oleyl-3-hydroxyethyl-imidazoline, 2-undecyl-3-hydroxyethyl-tetrahydropyrimidine and 2-oleyl-4-methyl-imidazoline.

The compounds of the formulae II, III and IV are known in the literature.

Suitable hydrocarbons are chlorinated aliphatic compounds, especially chlorinated low molecular weight alkanes or alkenes, bearing one or more chlorine atoms, for example methylene chloride, chloroform, carbon tetrachloride, ethylene chloride, trichloroethane or tetrachloroethylene, furthermore chlorinated aromatic compounds, for example chlorobenzene, dichlorobenzene, trichlorobenzene, tetrachlorobenzene as well as mixtures of different chlorinated hydrocarbons, furthermore aromatic hydrocarbons, for example benzene or alkylbenzenes, for example xylene or toluene.

Prior to being applied, the mixture according to the invention is advantageously diluted with water. For preparing a homogeneous dispersion, an emulsifier is added suitably, for example fatty acid polyglycol ester, alkylbenzene sulfonate, chlorinated paraffin sulfonate, sulfosuccinic acid ester, oxethylated alkylphenol or mixtures of these compounds.

A disinfectant preparation according to the present invention consists of a mixture of from 5 to 70% by weight, preferably 10 to 30% by weight, of a compound of the formula I, 95 to 30% by weight, preferably 90 to 70% by weight, of a chlorinated hydrocarbon or of a non chlorinated aromatic hydrocarbon or of a mixture of these hydrocarbons, and of from 0.2 to 0.9 mol, preferably 0.3 to 0.8 mol, of a compound of the formulae II, III or IV or of a mixture of these compounds, calculated on 1 mol of a compound of the formula I.

Prior to being used, the mixture according to the invention is advantageously diluted with water, optionally with the addition of from 0.1 to 30% by weight of an emulsifier, to a content of from 0.5 to 10% by volume.

The disinfectant preparation according to the invention is used for the disinfection of rooms and objects for the breeding and raising of domestic and commercially reared animals, especially for the disinfection of stables and their outruns.

The superiority of the mixtures according to the invention can be shown by the following method:

Oocysts of *Eimeria tenella* were collected from the excrement of hens previously infested and subjected to the test substances for the periods of time and at the concentrations as indicated in the following Table. The preparations were then washed once with dimethyl formamide and five times with water with centrifugation and the oocyst-containing sediment was used for the oral infection of chicken 4 days old. Each of 4 to 8 animals per concentration applied were administered about $2-3 \times 10^5$ treated oocysts.

After termination of the test, the average body weight per test group (absolute average weight increase, respectively weight decrease) was ascertained. The excrement were inspected every day during the whole test period and findings made and judged according to the following scheme:

| Excrement findings: | Judgement: |
|---|---|
| normally formed, solid, sporadically pultaceous (brown) | 1 |
| mainly normally formed, partly liquid, mucous (green-white) | 2 |
| mainly liquid, watery, minimal blood admixtures, mucous | 3 |
| liquid, mucous, distinct blood admixtures | 4 |

After termination of the test, the animals were killed with chloroform and the appendices were subjected to macroscopic and microscopic examination for pathological and anatomical changes.

The judgements of the pathological changes of the intestinal mucosa were determined as follows:

| Intestinal mucosa: | Judgement: |
|---|---|
| no special findings | 1 |
| swollen, gelatinous, glassy, catarrhal fibrinous inflammations | 2 |
| sporadically petechiae, local haemorrhagic inflammations | 3 |
| diffuse pink-turning to diffuse haemorrhagic inflammation, partly sanguinous intestinal contents. | 4 |

The number of the non-sporulated oocysts excreted in the excrements were counted.

| Number of oocysts per visual field | Judgement |
|---|---|
| 1 | 1 |
| 2–10 | 2 |
| 11–50 | 3 |
| 51–200 | 4 |
| 201–400 | 5 |
| over 400 | 6 |

The following Table shows the synergistic disinfection effect of the mixtures according to the invention, compared with mixtures of compounds of the formula I and of chlorinated organic solvents which contain no amines of the formulae II to IV.

Moreover the Table shows the superiority of the mixtures according to the invention, over the commercial preparation Dekaseptol (Trade Mark).

The concentrations are indicated in % by volume and are calculated on the content of the mixture according to the invention.

In the columns headed "excrement findings", "appendix findings" and "oocysts/unit field" the above judgements were used.

The following preparations were examined, by way of example:

(1)

20.0 g of

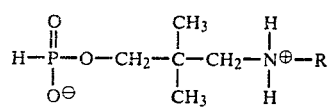

R=an alkyl radical of the coconut fatty acid
10.0 g of

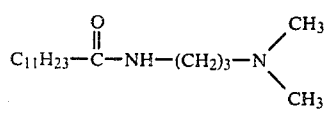

(which corresponds to 0.58 mol calculated on 1 mole of phosphite)
20.0 g of castor oil·40 moles of ethylene oxide
79.1 g of tetrachloroethylene (2)

20.0 g of

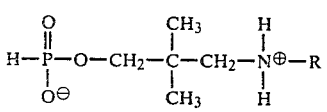

R=an alkyl radical of the coconut fatty acid
7.5 g of tallow fat propylene diamine·3 mols of ethylene oxide (corresponding to 0.58 mol per 1 mol of phosphite)
0.6 g of calcium salt of dodecylbenzenesulfonate
19.4 g of castor oil·36 mols of ethylene oxide
85.9 g of tetrachloroethylene (3)

20.0 g of

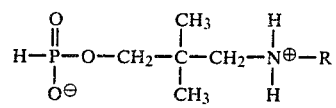

R=an alkyl radical of the coconut fatty acid
7.5 g of 2-undecylimidazoline (corresponding to 0.58 mol per 1 mol of phosphite)
2.7 g of calcium salt of dodecylbenzene-sulfonate
17.3 g of castor oil·36 moles of ethylene oxide
82.1 g of tetrachloroethylene (4) COMPARATIVE EXAMPLE 20.0 g of

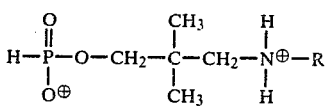

R=an alkyl radical of the coconut fatty acid
2.3 g of calcium salt of dodecylbenzene-sulfonate
10.2 g of castor oil·36 mols of ethylene oxide
108.5 g of tetrachloroethylene (5) COMPARATIVE EXAMPLE 20.0 g of

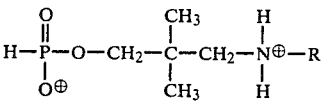

R=an alkyl radical of the coconut fatty acid
91.0 g of o-dichlorobenzene
8.0 g of castor oil·36 mols of ethylene oxide (6) COMPARATIVE EXAMPLE Dekaseptol (Trade Mark) (a mixture of chlorinated hydrocarbons and carbon sulfide in admixture with a special soap solution)

TABLE

Disinfection effect of different preparations against sporulated oocysts of *Eimeria tenella* aftr a 20 minutes suspension (suspension test in tap water)

| Preparation | Concentr. % by vol. | Excrement findings +d: 5,6,7 | Total number of surviving animals | Weight increase in g | Caecum section findings +d 7/4 animals | Oocysts/unit field +d 7/4 animals |
|---|---|---|---|---|---|---|
| 1. | 1 | 1 1 1 | 4/4 | + 22.3 | 1 1 1 1 | 0 0 0 0 |
|  | 2 | 1 1 1 | 4/4 | + 25.8 | 1 1 1 1 | 0 0 0 0 |
| 2. | 1 | 1 1 1 | 4/4 | + 23.7 | 1 1 1 1 | 0 0 0 0 |
|  | 2 | 1 1 1 | 4/4 | + 24.6 | 1 1 1 1 | 0 0 0 0 |
| 3. | 1 | 1 1 1 | 4/4 | + 22.8 | 1 1 1 1 | 0 0 0 0 |
|  | 2 | 1 1 1 | 4/4 | + 22.6 | 1 1 1 1 | 0 0 0 0 |
| 4. | 1 | 2 3 4 | 3/4 | + 11.8 | 2 3 3 4 | 5 4 4 5 |
|  | 2 | 2 2 2 | 3/4 | + 16.9 | 1 2 1 2 | 2 3 0 3 |
|  | 3 | 1 1 1 | 4/4 | + 16.3 | 1 1 1 1 | 0 0 0 1 |
| 5. | 1 | 3 2 3 | 4/4 | + 12.0 | 2 4 3 2 | 4 4 3 4 |
|  | 2 | 2 1 2 | 4/4 | + 15.8 | 1 2 2 1 | 3 2 2 2 |
|  | 3 | 1 1 1 | 4/4 | + 19.5 | 1 1 1 1 | 1 0 0 1 |
| 6 | 1 | 2 3 3 | 3/4 | + 10.3 | 3 3 3 4 | 5 6 4 2 |
|  | 2 | 2 2 3 | 3/4 | + 12.7 | 2 3 2 4 | 6 3 5 6 |
|  | 3 | 1 2 2 | 4/4 | + 16.2 | 1 1 2 2 | 3 0 0 0 |
|  | 6 | 1 1 1 | 4/4 | + 20.3 | 1 1 1 1 | 1 1 0 2 |
| Infection control | — | 2 4 4 | 0/4 | — | 4 4 4 4 | — |

TABLE-continued

Disinfection effect of different preparations against sporulated oocysts of *Eimeria tenella* aftr a 20 minutes suspension (suspension test in tap water)

| Preparation | Concentr. % by vol. | Excrement findings +d: 5,6,7 | Total number of surviving animals | Weight increase in g | Caecum section findings +d 7/4 animals | Oocysts/unit field +d 7/4 animals |
|---|---|---|---|---|---|---|
| Non infested control substance | — | 1 1 1 | 4/4 | − 24.3 | 1 1 1 1 | 0 0 0 0 |

*+d = day after infection

It can be seen from the table that the disinfection effect of the preparations 1, 2 and 3, after dispersion in water, at an aqueous concentration to be applied of 1% is distinctly superior to that of the preparations 4 and 5 which contain no amine. Only when used in a 3-fold higher concentration the preparation 4 has about the same disinfection effect against sporulated oocysts of Eimeria tenella as the preparations 1, 2 and 3. the preparations according to the invention in a 1% concentration to be applied have a pronounced superiority over Dekasepol used in the same concentration (factor 6).

We claim:

1. A disinfecting composition containing as its essential active ingredient an effective disinfecting amount of a mixture of a compound of the formula:

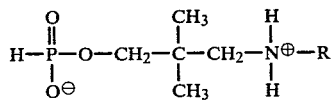

and a compound of the formula:

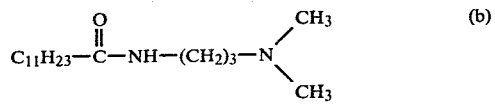

said mixture containing 0.2 to 0.9 mols of the compound of formula (b) per mol of the compound of formula (a) and R of formula (a) being an alkyl radical of coconut fatty acid.

2. The composition as defined in claim 1 which additionally contains a chlorinated hydrocarbon or a non-chlorinated aromatic hydrocarbon or combination thereof.

3. The composition as defined in claim 2 in which the relative proportions by weight of compound (a) and chlorinated hydrocarbon or non-chlorinated hydrocarbon or mixture thereof are about 5 to 70% and 95 to 30%, respectively, and the concentration of compound (b) is from about 0.2 to 0.9 mol per mol of compound (a).

4. The composition as defined in claim 2 in which the relative proportions by weight of compound (a) and chlorinated hydrocarbon or non-chlorinated hydrocarbon or mixture thereof are about 10 to 30% and 90 to 70%, respectively, and the concentration of compound (b) is from about 0.3 to 0.8 mol per mol of compound (a).

5. The method of disinfecting an object or area which comprises applying thereto an effective amount of a disinfecting composition as claimed in claim 1.

* * * * *